United States Patent [19]

Matsushita et al.

[11] Patent Number: 4,910,177
[45] Date of Patent: Mar. 20, 1990

[54] CATALYST FOR THE REDUCTION OF ALDEHYDES AND KETONES

[75] Inventors: Hajime Matsushita, Yokohama; Kyoko Takahashi, Tokyo; Makoto Shibagaki, Kawasaki, all of Japan

[73] Assignee: Japan Tobacco Inc., Minato, Japan

[21] Appl. No.: 185,041

[22] Filed: Apr. 22, 1988

Related U.S. Application Data

[62] Division of Ser. No. 30,155, Mar. 25, 1987, Pat. No. 4,783,559.

[30] Foreign Application Priority Data

Apr. 1, 1986 [JP] Japan ..................... 61-72569

[51] Int. Cl.$^4$ .......................... B01J 23/10; B01J 23/14
[52] U.S. Cl. ......................................... 502/65; 502/64; 502/182; 502/242; 502/263; 502/304; 502/352; 423/263; 423/618
[58] Field of Search ............... 502/304, 338, 350, 352, 502/353, 355, 182, 242, 263, 351, 64, 65; 423/263, 608, 618

[56] References Cited

U.S. PATENT DOCUMENTS

| | | | |
|---|---|---|---|
| 3,411,878 | 11/1968 | Graulier et al. | 423/628 X |
| 4,438,219 | 3/1984 | Brandenburg et al. | 502/355 X |
| 4,459,370 | 7/1984 | Vanderwal et al. | 502/338 |

FOREIGN PATENT DOCUMENTS

| | | | |
|---|---|---|---|
| 135145 | 3/1985 | European Pat. Off. | 502/353 |
| 152052 | 8/1985 | European Pat. Off. | 502/304 |
| 56-26547 | 3/1981 | Japan | 502/304 |
| 60-200827 | 10/1985 | Japan . | |

*Primary Examiner*—W. J. Shine
*Attorney, Agent, or Firm*—Ladas & Parry

[57] ABSTRACT

Disclosed is a process of reduction of aldehydes or ketones by means of reaction with alcohols, in the presence of a catalyst, to produce alcohols which correspond to said respective aldehyde or ketone. A solid of partially dehydrated one or more metal hydroxides whose metal is selected from the group consists of titanium, tin, ion, aluminum, cerium, and niobium is used as the catalyst. This process can be conducted either in a gas phase or in a liquid phase.

3 Claims, No Drawings

CATALYST FOR THE REDUCTION OF ALDEHYDES AND KETONES

This is a divisional of co-pending application Ser. No. 030,155 filed on Mar. 25, 1987, now U.S. Pat. No. 4,783,559.

BACKGROUND OF THE INVENTION

1. Field of the Invention

The present invention relates to a process of reduction of aldehydes or ketones, and more particularly, to a process of reduction which is conducted either in a gas phase or in a liquid phase by using a solid catalyst to obtain corresponding alcohols.

2. Description of the Prior Art

The Meerwein-Ponndorf-Verley reduction process is well known and has been widely used for reduction of aldehydes or ketones, to obtain corresponding alcohols.

In this process, aldehyde or ketone is subjected to reaction in the presence of metal alcoholate and alcohol. A number of combinations of metal alcoholates and alcohols have been tried, in order to attain an optimum result, of which the combination of aluminium isopropoxide and 2-propanol has proved to be most effective, due to it having the following advantages:

Firstly, the reaction using aluminium isopropoxide and 2-propanol is accompanied by hardly any adverse side reaction, such as aldol condensation.

Secondly, since aluminium isopropoxide is soluble not only in alcohol but also in hydrocarbon compounds, the reaction can be conducted in a homogeneous state.

Thirdly, since the reaction proceeds quite rapidly, a high yield of the reduction product can be realized.

Nevertheless, the process is accompanied by certain disadvantages. Since the above-described known process consists in a homogeneous reaction, it requires complex and painstaking follow-up operations including hydrolysis, extraction using an organic solvent, dehydration and distillation, so as to isolate the product after the completion of the reaction.

Moreover, since the carbonyl group of the starting compound is converted to a hydroxyl group in the final product of the reaction, its hydrophilic property is significantly enhanced as compared with that of the starting compound.

Therefore, the ratio of the part of the product that can be extracted from the aqueous layer, by means of an organic solvent, to the overall product will be inevitably held at a relatively low level, resulting in a poor yield of the reaction product.

Besides, whereas active aluminium isopropoxide is of trimer type, any aluminium isopropoxide now available in the market and/or which is supplied in a crystal form is of tetramer type and has poor catalytic activity. Therefore, a catalyst to be used for this process should be prepared immediately before the initiation of the reduction process.

What is more, catalysts which can be used for this process require particular care in their storage, because during storage they can be gradually hydrolyzed by water moisture in the air, and become aluminium hydroxide which has no catalytic actively.

Furthermore, in this process, catalyst which has been used should be hydrolyzed so as to isolate the product from the reaction system, upon completion of the reaction. As a result, it cannot be used further.

SUMMARY OF THE INVENTION

It is therefore the object of the present invention to provide a process of reduction of aldehydes or ketones, in the presence of a catalyst, to obtain corresponding alcohols at a high yield, characterized in that the process uses a catalyst which has high catalytic activity and can be used in a heterogeneous system at relatively low cost, that neither requires any complex and painstaking follow-up operations for isolation of the product nor is accompanied by any deactivation problems due to water, and where the reaction can be conducted either in a gas phase or in a liquid phase.

To attain the above-mentioned object, the present invention provides a process of reduction of aldehydes or ketones by reaction with alcohols, in the presence of a catalyst, to obtain corresponding alcohols, characterized in that the catalyst is a solid of one or more partially dehydrated metal hydroxides whose metal is selected from the group consisting of titanium, tin, iron, aluminium, cerium, and niobium.

DETAILED DESCRIPTION OF THE PREFERRED EMBODIMENTS

The present invention is characterized in that the catalyst which is used in the above process is a solid of one or more partially dehydrated metal hydroxides whose metal is selected from the group consisting of titanium, tin, iron, aluminium, cerium, and niobium. It should be noted that the inventors of the present invention have already found that a partially dehydrated solid of zirconium hydroxide can be used as a catalyst for the above process, and have already applied for a patent therefor (PCT/JP 86/00460).

The partially dehydrated metal hydroxide can be obtained by thermally treating the corresponding metal hydroxide under the condition in which the metal hydroxide has not yet fully dehydrated to become the corresponding metal oxide. In the case of zirconium, as described in the above international patent application, whereas zirconium hydroxide is completely dehydrated to become zirconia ($ZrO_2$) when thermally treated at 500° C. under atmospheric pressure, it will become partially dehydrated if treated at around 300° C. and the partially dehydrated state is maintained in a stable manner. In other words, when zirconium hydroxide is treated at an intermediate temperature of about 300° C., the overall reaction system shows a reduction of weight by some 17% within one hour from the start of the reaction, the weight thereafter remaining at about the same level. This phenomenon can be observed not only in the partial dehydration of zirconium hydroxide but also in any corresponding partial dehydration of hydroxide of metals other than zirconium.

The catalyst compounds as described above are white and highly solid but amorphous. Hence, X-ray diffraction cannot be used for structural analysis of the materials, and as a result, their exact chemical structures are not known to date. However, the fact that these metal hydroxides can be partially dehydrated suggests that every product compound has a metal-oxygen-metal bonding, and that the hydroxyl groups which are directly bonded to the metal atom in the original material still remain. The catalyst materials described above are soluble neither in organic solvents such as alcohol nor in water, and are stable enough to function as heterogeneous catalysts. It is known that the materials have a relatively low surface acidity and ion exchangeability in the presence of various sources of ions.

The catalysts can be prepared in a relatively simple and inexpensive way by converting oxides, chlorides, or salts of their respective metals (which are found abundantly in nature as mineral resources) to hydroxides, which are in turn thermally treated in the respective predetermined conditions. This confers a significant advantage on the catalysts of the present invention, over any existing metal alcoholate catalysts. Furthermore, it should be noted that the catalyst materials of the present invention can be crushed to particles of suitable sizes for use or, alternatively, they can be carried by appropriate carrier substrate including alumina, active charcoal, silica gel, silica-alumina, and zeolite.

The process of reduction of aldehydes or ketones according to the present invention can be conducted either in a gas phase or in a liquid phase.

When the process of the present invention is conducted in a liquid phase, it may be regarded simply as a process which is similar to the known Meerwein-Ponndorf-Verley process in which the catalyst of metal alcoholate is replaced by an catalyst of a solid of partially dehydrated metal hydroxide. Hence, any of the facilities and techniques which are used for the reduction of aldehydes or ketones in the known process may be used unchanged for the process of the present invention. For example, a distillation facility is used in the known process to separate acetone, which is produced as a by-product, in order to accelerate the reaction, and it can be used in the process according to the present invention, without any alterations thereto.

When reduction of aldehydes or ketones is conducted by the process of the present invention, in a liquid phase, 0.1 to 10 g, preferably 1 to 3 g, of any one of the above-mentioned catalyst materials is used for every 10 mmol of aldhyde or ketone. The catalyst is dissolved in 0.5 to 20 ml, preferably 5 to 10 ml, of 2-propanol or any other suitable alcohol, and the solution is mixed with the given aldehyde or ketone, the resultant mixture is then heated. During the reaction, acetone which is produced as a by-product is desirably removed by distillation, so that the speed of the reaction may be accelerated.

When the reaction is completed, the catalyst material is collected by means of filtration. The filtered solution is dried and then distilled to isolate the product. Depending on the circumstances, the product can be alternatively isolated through crystallization, directly from the solution. The collected catalyst material may be reutilized after being washed with ethanol and water, and then dried.

Since the above-described catalysts which can be used for the process of the present invention are highly active, but stable and hard amorphous substances, the process of the present invention can be realized in a gas phase, in the following way:

Firstly, a given amount of any of the above-described catalyst materials is placed in a suitable reaction tube, to provide a catalyst bed. Then, the reaction tube is heated to a temperature suitable for the expected reaction to take place; normally somewhere between 70° C. and 200° C. After heating the tube, a mixture of aldehyde or ketone and alcohol is continuously fed into the reaction tube, in such a manner that the mixture comes into contact with the catalyst bed.

Air, nitrogen, helium, argon, or any other appropriate carrier gas may be used to feed in the mixture of the above-mentioned materials. A cooling device using water, ice, or some other cooling medium is provided at the exit of the reaction tube, so as to liquefy the gaseous reaction product and collect it. Although the collected liquid may contain a certain amount of residual materials and, in some case, of by-products other than the reaction product, the latter can be easily isolated, as in the case of reaction carried out in a liquid phase.

The process of reduction of aldehydes or ketones according to the present invention is free from the problems which are associated with the conventional homogeneous catalyst reaction processes. Consequently, the corresponding alcohols can be produced at a relatively high yield. Moreover, the catalytic activity of the catalysts which can be used in the process according to the present invention will not deteriorate even when they are used continuously over a long period of time. Hence, the catalysts can be repeatedly used, so with the result that the process is free from emission of industrial wastes, thereby making it highly advantageous for industrial applications.

Some examples of the preparation of catalysts to be used for the process of the present invention and of the reduction of aldehydes or ketones, according thereto will now be described.

EXAMPLE 1

(Preparation of an Catalyst)

190 g of titanium tetrachloride was added 4 l of deionized water and then 28% aqueous ammonia was gradually added to the above mixture until pH of the solution was reached to 7.0. As the result, hydrated gel of the titanium hydroxide was produced. The hydrated gel was separated through filtration by using a Buchner funnel and then washed with deionized water repeatedly until no chloride ion was detected in the filtered solution. The gel thus obtained was then cut to small pieces by using a knife and they were scattered on a glass plate and dried at room temperature. When the dried pieces were introduced into deionized water, they were fiercely cracked to granules of various granular sizes. The mixture of water and granules were then filtered and the granules of titanium hydroxide which were separated from the water were dried in a enamelled vat at room temperature. The dried granules of titanium hydroxide were then sieved and those having the granular sizes between 24 and 60 meshes were selected. The selected granules were thermally treated in a drying container at 300° C. for three hours thereby obtaining a solid of partially dehydrated titanium hydroxide.

EXAMPLE 2

(Preparation of a Catalyst)

261 g of tin tetrachloride was added to 4 l of deionized water drop by drop. Immediately thereafter, 28% aqueous ammonia was gradually added to the mixture until pH=7.0 was attained, thereby producing hydrated gel of tin hydroxide. The produced hydrated gel was then separated from the water through filtration using a Buchner funnel and the obtained hydrated gel was washed with deionized water until no chloride ion was detected in the filtered water. The gel thus obtained was then cut to small pieces by using a knife and they were scattered on a glass plate and dried at room temperature. When the dried pieces were introduced into deionized water, they were fiercely cracked to granules of various sizes. The mixture of water and granules were then filtered and the granules which were separated from the water were then dried in a enamelled vat at room temperature. The dried granules of tin hydroxide were then sieved and those having the granular sizes between 24 and 60 meshes were selected. The selected granules were thermally treated in a drying container at 300° C. for three hours thereby obtaining a solid of partially dehydrated thin hydroxide.

EXAMPLE 3

(Preparation of a Catalyst)

270 g of ferric chloride ($FeCl_3.6H_2O$) was added drop by drop to 4 l of deionized water. Immediately thereafter, 28% aqueous ammonia was slowly added to the above mixture until pH=7.0 was attained, then hydrated gel of ferric hydroxide was produced. The produced hydrated gel was separated through filtration by using a Buchner funnel and then washed with deionized water repeatedly until no chloride ion was detected in the filtered solution. The hydrated gel thus obtained was cut to small pieces by using a knife and they were scattered on a glass plate and dried at room temperature. When the dried pieces were introduced into deionized water, they were fiercely cracked to granules of various sizes. The mixture of water and granules were then filtered and the granules which were separated from the water were dried in a enamelled vat at room temperature. The dried granules of ferric hydroxide were then sieved and those having the granular sizes between 24 and 60 meshes were selected. The selected granules were thermally treated in a drying container at 300° C. for three hours thereby obtaining a solid of partially dehydrated ferric hydroxide.

EXAMPLE 4

(Preparation of a Catalyst)

328 g of sodium aluminate was dissolved in 3 l of deionized water. Then 2 l of aqueous solution containing 336 g of sodium hydrogencarbonate was gradually added to the above solution while it was kept stirring until hydrated gel of the sodium aluminate was produced. The produced hydrated gel was separated through filtration and then washed with deionized water repeatedly until the pH of the washing water reached 7.5. The hydrated gel thus obtained was then cut to small pieces by using a knife and they were scattered on a glass plate and dried at room temperature. When the dried pieces were introduced into deionized water, they were fiercely cracked to granules of various sizes. The mixture of water and granules were then filtered and the granules of aluminium hydroxide which were separated from the water were then dried in a enamelled vat at room temperature. The dried granules of aluminium hydroxide were then sieved and those having the granular sizes between 24 and 60 meshes were selected. The selected granules were thermally treated in a drying container at 300° for three hours thereby obtaining a solid of partially dehydrated aluminium hydroxide.

EXAMPLE 5

(Preparation of a Catalyst)

186 g of cerous chloride ($Ce_2O_3.7H_2O$) was dissolved in 2 l of deionized water and then 25 ml of 35% hydrogen peroxide solution was added to the above mixture for oxidization. Thereafter, 28% aqueous ammonia was gradually added to the oxidized solution while the latter was being stirred until the pH of the solution reached 7.0, then hydrated gel of ceric hydroxide was produced. The produced hydrated gel was separated through filtration and then washed with deionized water repeatedly until no chloride ion was detected in the washing water. The gel thus obtained was then cut to small pieces by using a knife and they were scattered on a glass plate and dried at room temperature. When the dried pieces were introduced into deionized water, they were fiercely cracked to granules of various granular size. The mixture of water and granules were then filtered and the granules of ceric hydroxide which were separated from the water were dried in a enamelled vat at room temperature. The dried granules of ceric hydroxide were then sieved and those having the granular size between 24 and 60 meshes were selected. The selected granules were thermally treated in a drying container at 300° C. for three hours thereby obtaining a solid of partially dehydrated ceric hydroxide.

EXAMPLE 6

(Preparation of an Catalyst)

50 g of niobium pentachloride anhydride was dissolved in 100 cc of concentrated hydrochloric acid and then the solution was diluted with 2 l of deionized water. The diluted solution was boiled for two hours thereby producing hydrated gel of niobium (V) hydroxide. The produced hydrated gel was washed with deionized water until no chloride ion was detected in the washing water. The hydrated gel thus obtained was then cut to small pieces by using a knife and they were scattered on a glass plate and dried at room temperature. When the dried pieces were introduced into deionized water, they were fiercely cracked to granules of various sizes. The mixture of water and granules were then filtered and the granules of niobium (V) hydroxide which were separated from the water were dried in an enamelled vat at room temperature. The dried granules of niobium (V) hydroxide were then sieved and those having the granular sizes between 24 and 60 meshes were selected. The selected granules were thermally treated in a drying container at 300° C. for three hours thereby obtaining a solid of partially dehydrated niobium hydroxide.

EXAMPLES 7-21

(Reduction Reactions: Gas Phase)

Using a variety of partially dehydrated metal hydroxides which were prepared in such ways as described in Examples 1-6 above, reduction of aldehydes or ketones was conducted as follows.

The amount of the catalyst used in every example was 2 g.

The prescribed amount of any one of the catalysts as cited above was put into a glass tube (inner diameter=4 mm, outer diameter=6 mm) and the tube was fixedly mounted on an electric furnace. The glass tube served as a reactor vessel and liquid mixture of alcohol and an aldehyde or ketone which was to be reduced was fed into the tube by means of a micro-feeder at a rate of 5 ml/hour. A nitrogen gas flow (0.5 ml/sec) was utilized to carry the material. The alcohol used was cyclohexanol in Example 13, ethanol in Example 14 and 2-propanol in the rest of the examples. The mol ratio of aldehyde or ketone to alcohol was 1:10 except for that of Example 10, in which the ratio of ketone to alcohol was 1:30.

The supplied material substances were gasified in the glass tube and put into contact with the catalyst for reaction. Then the reaction product came flowing out of the tube. The gaseous product was cooled with water for liquefaction for ease of collection and the liquefied product was subjected to a gas chromatography analysis to determine the conversion rate and the yield. Table 1 shows the results of the experiments conducted for the examples.

EXAMPLES 22-30

(Reduction Reactions: Liquid Phase)

Using a variety of partially dehydrated metal hydroxides which had been prepared in such ways as described in Example 1-6 above, aldehydes and ketones were reduced in a manner as described below.

The amount of the catalyst used in every example was 2 g.

The prescribed amount of any one of the catalysts as cited above was put into a flask having the volume of 50 ml which was equipped with a reflux device. 10 ml of

TABLE 1

Reduction Reactions in a Gas Phase

| No. | catalyst | material | reaction temperature (%) | product | conversion rate (%) | yield (%) |
|---|---|---|---|---|---|---|
| 7 | Example 1 (titanium) | cyclohexanone | 100 | cyclohexanol | 22 | 15 |
| 8 | Example 1 (titanium) | " | 150 | " | 44 | 44 |
| 9 | Example 1 (titanium) | " | 200 | " | 99 | 92 |
| 10 | Example 1 (titanium) | " | 150 | " | 62 | 62 |
| 11 | Example 1 (titanium) | acetophenone | 150 | 1-phenylethanol | 67 | 67 |
| 12 | Example 1 (titanium) | benzaldehyde | 150 | benzyl alcohol | 82 | 41 |
| 13 | Example 1 (titanium) | " | 150 | " | 94 | 36 |
| 14 | Example 1 (titanium) | " | 150 | " | 39 | 30 |
| 15 | Example 2 (tin) | cyclohexanone | 100 | cyclohexanol | 60 | 60 |
| 16 | Example 2 (tin) | methyl isobutyl ketone | 150 | methyl isobutyl carbinol | 58 | 52 |
| 17 | Example 3 (iron) | cyclohexanone | 100 | cyclohexanol | 27 | 27 |
| 18 | Example 4 (cerium) | cyclohexanone | 100 | cyclohexanol | 72 | 68 |
| 19 | Example 4 (cerium) | methyl isobutyl ketone | 150 | methyl isobutyl carbinol | 65 | 55 |
| 20 | Example 5 (aluminium) | cyclohexanone | 100 | cyclohexanol | 39 | 39 |
| 21 | Example 6 (niobium) | " | 100 | " | 20 | 14 | liquid mixture of alcohol and an aldehyde or ketone which was to be reduced was put into the flask and set for reaction by heating with a mantle heater for five hours, during which the liquid mixture was slowly reflowed. The alcohol used was cyclohexanol in Example 22 and 2-propanol in the rest of the examples. The mol ratio of aldehyde or ketone to alcohol was 1:10. In Example 23, an equivalent amount of xylene was added to the reaction liquid and the mixture was subjected to reflux.

After completion of reaction, a small amount of the liquid product was taken out as sample and subjected to a gas chromatography analysis to determine the conversion rate and the yield. Table 2 shows the results of the experiments conducted for the examples.

What is claimed is:

1. A catalyst in the presence of which an aldehyde or ketone is reacted with an alcohol to obtain an alcohol corresponding to the aldehyde or ketone, wherein said catalyst is a solid of one or more partially dehydrated metal hydroxides whose metal is selected from the group consisting of tin and cerium.

2. A catalyst according to claim 1, wherein said solid, pulverized into grains having a suitable size, is used without further modification.

3. A catalyst according to claim 1, wherein said solid is carried on carrier selected from the group consisting of alumina, active charcoal, silica gel, silica-aluminum and zeolite.

TABLE 2

| No. | catalyst | material | product | conversion rate (%) | yield (%) |
|---|---|---|---|---|---|
| | | Reduction Reactions in a Liquid Phase | | | |
| 22 | Example 1 (titanium) | cyclohexanone (=O) | cyclohexanol (-OH) | 17 | 14 |
| 23 | Example 1 (titanium) | " | " | 20 | 20 |
| 24 | Example 1 (titanium) | benzaldehyde (-CHO) | benzyl alcohol (-CH$_2$OH) | 40 | 15 |
| 25 | Example 1 (titanium) | " | " | 99 | 40 |
| 26 | Example 2 (tin) | cyclohexanone (=O) | cyclohexanol (-OH) | 20 | 20 |
| 27 | Example 3 (iron) | " | " | 25 | 25 |
| 28 | Example 4 (cerium) | " | " | 45 | 32 |
| 29 | Example 5 (aluminium) | " | " | 6 | 6 |
| 30 | Example 6 (niobium) | " | " | 17 | 6 |

* * * * *